US011162928B2

(12) United States Patent
Goel et al.

(10) Patent No.: US 11,162,928 B2
(45) Date of Patent: Nov. 2, 2021

(54) HUMIDITY CORRECTION METHOD IN THERMISTOR BASED GAS SENSING PLATFORM

(71) Applicant: INVENSENSE, INC., San Jose, CA (US)

(72) Inventors: Nishit Goel, Allston, MA (US); Stephen Bart, West Newton, MA (US)

(73) Assignee: INVENSENSE, INC., San Jose, CA (US)

( * ) Notice: Subject to any disclaimer, the term of this patent is extended or adjusted under 35 U.S.C. 154(b) by 207 days.

(21) Appl. No.: 16/672,738

(22) Filed: Nov. 4, 2019

(65) Prior Publication Data
US 2021/0132014 A1  May 6, 2021

(51) Int. Cl.
*G01N 33/00* (2006.01)
(52) U.S. Cl.
CPC ......... *G01N 33/006* (2013.01); *G01N 33/004* (2013.01); *G01N 33/0037* (2013.01)
(58) Field of Classification Search
CPC ............ G01N 27/407; G01N 27/4074; G01N 33/0037; G01N 33/004; G01N 33/0042; G01N 33/0044; G01N 33/0045; G01N 33/005; G01N 33/0052; G01N 33/0054; G01N 33/006
See application file for complete search history.

(56) References Cited

U.S. PATENT DOCUMENTS

| | | | |
|---|---|---|---|
| 3,720,093 A | 3/1973 | Gill | |
| 4,760,351 A * | 7/1988 | Newell | G04F 5/06 310/320 |
| 4,958,513 A * | 9/1990 | Yasunaga | B60H 1/008 73/23.2 |
| 5,088,314 A * | 2/1992 | Takashi | G01N 33/0063 236/49.3 |
| 5,418,131 A | 5/1995 | Butts | |

(Continued)

FOREIGN PATENT DOCUMENTS

GB       766590       1/1957
JP    58011847 A  *  1/1983

(Continued)

OTHER PUBLICATIONS

ESPACENET Machine Translation of JP-58011847 A Which Originally Published on Jan. 22, 1983. (Year: 1983).*

(Continued)

*Primary Examiner* — David A. Rogers
(74) *Attorney, Agent, or Firm* — Haley Guiliano LLP; Joshua V. Van Hoven; Stefan D. Osterbur

(57) ABSTRACT

A gas sensor may include a plurality of elements that are responsive to particular gases based at least in part on the temperature of the temperature sensitive element. A first of the elements may be a gas detection element heated to a temperature at which it is responsive to a gas of interest. A plurality of additional elements may be configured in a reference element network and heated to a temperature at which they are not responsive to the gas of interest but are instead responsive to other effects such as humidity. The reference element network output may be used to remove the other effects (e.g., humidity) from the gas detection element output.

20 Claims, 7 Drawing Sheets

(56) References Cited

U.S. PATENT DOCUMENTS

| | | | | |
|---|---|---|---|---|
| 5,521,099 A * | 5/1996 | Glaunsinger | G01N 27/002 | 422/88 |
| 6,241,873 B1 * | 6/2001 | Namba | G01N 27/4074 | 204/421 |
| 7,028,530 B2 * | 4/2006 | Katsuki | G01N 33/005 | 73/25.03 |
| 7,341,694 B2 * | 3/2008 | Nishiyama | G01N 27/4075 | 422/90 |
| 7,460,958 B2 * | 12/2008 | Walsh | G01N 33/0034 | 702/24 |
| 8,683,845 B2 * | 4/2014 | Fleischer | G01N 27/4143 | 73/23.21 |
| 9,052,270 B2 * | 6/2015 | Wiesner | G01N 27/12 | |
| 9,261,472 B2 * | 2/2016 | Kimura | G01N 25/4873 | |
| 9,523,665 B2 * | 12/2016 | Fleischer | G01N 27/4143 | |
| 9,976,976 B2 * | 5/2018 | Nakano | F02M 35/1038 | |
| 10,436,737 B2 * | 10/2019 | Sussner | G01N 29/00 | |
| 10,578,572 B2 * | 3/2020 | Liu | G01N 27/14 | |
| 10,598,621 B2 * | 3/2020 | Liu | G01N 27/04 | |
| 10,794,728 B2 * | 10/2020 | Teskey | G01C 25/005 | |
| 10,935,509 B2 * | 3/2021 | Liu | G01N 27/18 | |
| 2003/0131653 A1 | 7/2003 | Bair, III et al. | | |
| 2004/0132202 A1 * | 7/2004 | Nishiyama | G01N 27/4075 | 436/113 |
| 2005/0228596 A1 * | 10/2005 | Shoji | G01N 27/18 | 702/24 |
| 2006/0042965 A1 * | 3/2006 | Sasaki | G01N 27/16 | 205/784 |
| 2009/0026076 A1 * | 1/2009 | Yang | G01N 33/0037 | 204/412 |
| 2010/0279425 A1 * | 11/2010 | Patel | G01N 33/0054 | 436/149 |
| 2010/0323258 A1 * | 12/2010 | Blackburn | G01N 27/30 | 429/428 |
| 2011/0048108 A1 * | 3/2011 | Yamagishi | G01N 33/0037 | 73/31.06 |
| 2011/0146382 A1 * | 6/2011 | Fleischer | G01N 27/4143 | 73/25.01 |
| 2011/0158854 A1 * | 6/2011 | Yamagishi | G01N 33/005 | 422/83 |
| 2012/0272720 A1 * | 11/2012 | Wiesner | G01N 27/12 | 73/31.05 |
| 2013/0209315 A1 * | 8/2013 | Kimura | G01N 25/4826 | 422/88 |
| 2013/0233728 A1 * | 9/2013 | Day | C04B 35/50 | 205/780.5 |
| 2014/0109649 A1 * | 4/2014 | Fleischer | G01N 27/4143 | 73/31.02 |
| 2015/0253275 A1 * | 9/2015 | Blackburn | H01M 8/04537 | 205/775 |
| 2016/0139071 A1 * | 5/2016 | Nakano | G01F 1/692 | 73/23.31 |
| 2016/0290961 A1 * | 10/2016 | Aoki | G01N 27/4074 | |
| 2017/0052161 A1 * | 2/2017 | Liu | G01N 33/0027 | |
| 2017/0067841 A1 * | 3/2017 | Liu | G01N 27/046 | |
| 2017/0082648 A1 * | 3/2017 | Katginari | G01P 1/006 | |
| 2017/0205368 A1 * | 7/2017 | Liu | G01N 27/046 | |
| 2018/0202961 A1 * | 7/2018 | Sussner | G01N 29/036 | |
| 2018/0292338 A1 * | 10/2018 | Liu | G01N 33/0073 | |
| 2018/0340901 A1 * | 11/2018 | Liu | G01N 27/046 | |
| 2019/0072523 A1 * | 3/2019 | Britt | G01N 29/022 | |
| 2021/0003525 A1 * | 1/2021 | Kaita | G01N 33/004 | |

FOREIGN PATENT DOCUMENTS

| | | | |
|---|---|---|---|
| JP | 01199144 A | * | 8/1989 |
| JP | 2016170161 A | * | 9/2016 |

OTHER PUBLICATIONS

ESPACENET Machine Translation of JP-2016170161 A Which Originally Published on Sep. 23, 2016. (Year: 2016).*
ESPACENET Machine Translation of JP-H-01199144 A Which Originally Published on Aug. 10, 1989. (Year: 1989).*

* cited by examiner

HUMIDITY CORRECTION METHOD IN THERMISTOR BASED GAS SENSING PLATFORM

BACKGROUND

Semiconductor-based gas sensors may utilize components that change their electrical, chemical and/or mechanical behavior in response to the presence of particular gases. The response of the gas-sensitive components may vary based on a number of factors, such as the temperature of the gas-sensitive components and the presence of gases or environmental conditions that also modify the response of the gas-sensitive components. In many end-use applications, gas sensors are subject to a variety of environments and operating conditions, some of which may compromise the accuracy of the gas sensor due to other impacts on sensor output overwhelming the contribution of the particular gas to the sensor output.

SUMMARY

In an embodiment of the present disclosure, a sensor for measuring a concentration of a gas of interest may comprise a gas detection element and a reference element network comprising a plurality of reference elements, wherein each reference element of the plurality of reference elements is coupled to another reference element of the plurality of reference elements. The sensor may further comprise one or more heating elements, wherein the one or more heating elements cause the gas detection element to operate at a first temperature at which the gas detection element is sensitive to the gas of interest and wherein the one or more heating elements cause the plurality of reference elements to operate at a second temperature at which the reference element network is not sensitive to the gas of interest. The sensor may further comprise processing circuitry coupled to the gas detection element and the reference element network, wherein the processing circuitry is configured to determine a value corresponding to the concentration of the gas of interest based on one or more signals received from the gas detection element and the reference element network.

In an embodiment of the present disclosure, a method for measuring a concentration of a gas of interest may comprise applying, by a first heating element, a first temperature to a gas detection element, wherein the gas detection element is sensitive to the gas of interest at the first temperature. The method may further comprise applying, by at least one second heating element, a second temperature to a reference element network comprising a plurality of reference elements, wherein the reference element network is not sensitive to the gas of interest at the second temperature. The method may further comprise determining, by processing circuitry coupled to the gas detection element and the reference element network, a value corresponding to the concentration of the gas of interest based on one or more signals received from the gas detection element and the reference element network.

In an embodiment of the present disclosure, a sensor for measuring a concentration of a gas of interest may comprise a gas detection element and a reference element network coupled to the gas detection element at a connecting node, the reference element network comprising a plurality of reference elements. The sensor may further comprise one or more heating elements, wherein the one or more heating elements cause the gas detection element to operate at a first temperature at which the gas detection element is sensitive to the gas of interest and wherein the one or more heating elements cause the plurality of reference elements to operate at a second temperature at which the reference element network is sensitive to humidity and is not sensitive to the gas of interest. The sensor may further comprise processing circuitry coupled to the connecting node, wherein the processing circuitry is configured to determine a value corresponding to the concentration of the gas of interest based on an output signal from the connecting node.

BRIEF DESCRIPTION OF THE DRAWINGS

The above and other features of the present disclosure, its nature, and various advantages will be more apparent upon consideration of the following detailed description, taken in conjunction with the accompanying drawings in which.

DETAILED DESCRIPTION OF DRAWINGS

Figure 1:
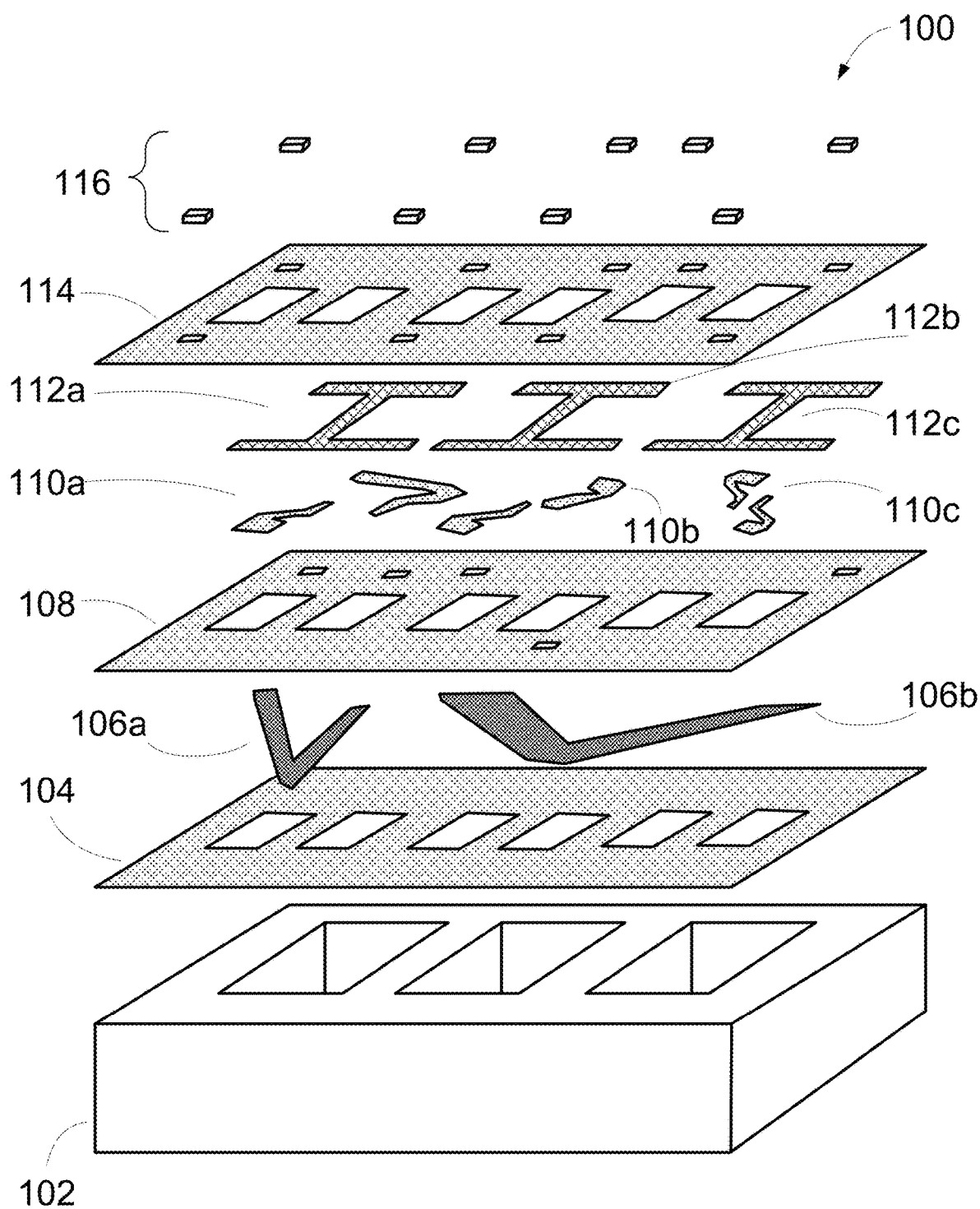
FIG. 1 depicts an exploded view of an exemplary gas sensor in accordance with some embodiments of the present disclosure.

An exemplary gas sensor is fabricated using semiconductor processes and includes one or more sensing elements such as thermistors. Physical properties of the materials of the sensing elements are sensitive to changes in the concentration of particular gases that interact with the sensor element material. The response may be electrical, chemical, and/or mechanical. In an exemplary embodiment of a thermistor-type sensing element, a particular thermistor material (e.g., MnCoNi oxide, $BaTiO_3$, NiO, or oxides of manganese, nickel, cobalt, and/or iron) may be sensitive to a gas such as carbon monoxide (CO) or carbon dioxide ($CO_2$), such that the temperature and resistance of the thermistor changes (e.g., increases) in proportion to the concentration of the gas of interest in the volume of air being tested. The sensing element (e.g., a thermistor) that is sensing the gas of interest (i.e., a "gas detection element") may also be sensitive to other conditions, such as water vapor that creates humidity within the volume of air.

The response of sensing elements is also dependent upon a temperature of the sensing element. Sensing elements may be heated to particular temperatures at which they are sensitive to concentrations of particular gases of interest and less sensitive to other gases or environmental conditions. In an exemplary embodiment of thermistors, heaters may be located proximate the thermistors such that the thermistor temperatures can be set to a temperature at which further changes in resistance and temperature are likely the result of the gas of interest. In some embodiments the heaters may be controllable such that the temperature of the gas sensing elements may be changed (e.g., to sense different gases) or tuned (e.g., to better sense the gas of interest under particular conditions).

A gas detection element may be heated to a temperature at which it is sensitive to the gas of interest, which may result in changes in gas detection element (e.g., resistance) that can be measured (e.g., based on a voltage, current, or other values or based on a component changing state in response to the change in the gas detection element) as the concentration of the gas of interest (e.g., CO or $CO_2$) changes. The gas detection element may nonetheless also be sensitive to other conditions (e.g., $H_2O$ vapor or humidity) even at the selected temperature. Additional sensing elements may be provided to counteract the effects of the other conditions on the gas detection element, for example, by directly measuring the other conditions that impact the output of the gas detection element.

In an embodiment of the present disclosure, a plurality of additional sensing elements may be utilized as reference elements of a reference element network that are responsive to the other conditions that impact the output of the gas detection element. For example, reference elements may be heated to a different temperature that is primarily responsive to the other conditions that impact the output of the gas detection element (e.g., humidity) and at which there is little or no response to the gas of interest (e.g., CO or $CO_2$). The reference elements and the gas detection element (e.g., thermistors) may be sized and configured, and the respective temperatures of the reference elements and gas detection element may be set, such that the response of the reference elements to the other conditions substantially offsets the response of the gas detection element to the other conditions. In this manner, the other condition or conditions that obscure the output of the gas detection element related to the gas of interest may be removed and the resulting output may correspond to the gas of interest only.

The reference elements may be configured into a reference element network and may interact with the output of the gas detection element. In an exemplary embodiment, the reference element network may include two reference elements that are connected to each other in parallel and that are coupled to the gas detection element to form a voltage divider. Additional circuit elements such as one or more trim resistors may also be included within the voltage divider. A common connecting node where the gas detection element is coupled to the reference element network may be monitored. Proper selection, configuration, and heating of the reference elements and the gas detection element may result in an output at the node that does not change in response to the other conditions (e.g., any change to the resistance of the thermistor of the gas detection element due to humidity is offset by a corresponding change to the thermistor of the reference element network due to humidity) but that does change in response to the gas of interest (e.g., the resistance of the thermistor of the gas detection element changes in response to the gas of interest but the resistance of the thermistor of the reference element network is not responsive to the gas of interest).

In some embodiments, the reference element network may include other configurations such as multiple parallel and series paths that may be switched into the circuit depending on particular other conditions that are being removed from the output of the gas detection element, the size and/or material of the gas detection element, the temperature of the gas detection element, or the gas or gases that are being sensed by the gas detection element. The operation of the gas sensor may be further optimized by tuning the temperatures applied to the gas detection element and/or reference element network for particular conditions or gases to be sensed.

FIG. 1 depicts an exploded view of an exemplary gas sensor in accordance with some embodiments of the present disclosure. Although a particular gas sensor having a certain set of materials, components, gas sensitivity, sensor type, shape and configuration is depicted in FIG. 1, it will be understood that these parameters may be varied and further that the present invention is applicable to other types of gas sensors or to combinations of gas sensors. For example, while the embodiment described in FIG. 1 may include multiple heating elements within a single device to apply different operating temperatures to gas detection elements and reference elements respectively, in some embodiments multiple gas sensors each having a single heating element may be located in proximity to each other such that one or more gas sensors applies a first operating temperature to a gas detection element while one or more additional gas sensors applies a second operating temperature to the reference elements. Further, it will be understood that the present invention may be applied to other types of gas sensors that are temperature sensitive, including but not limited to those described in commonly owned U.S. patent application Ser. No. 15/000,729, filed Jan. 19, 2016 and entitled "CMOS Integrated Microheater for a Gas Sensor Device" and U.S. patent application Ser. No. 15/484,864, filed Apr. 11, 2017 and entitled "Gas Sensing Method and Device," both of which are incorporated by reference herein in their entireties.

An exemplary gas sensor 100 may include a plurality of components and layers, such as wafer 102, thermal film 104, heating elements 106a-106b, insulating film 108, electrodes 110a-110c, thermistors 112a-112c, insulating film 114, and electrode pads 116. Although these particular components are described and depicted in a particular combination and configuration in FIG. 1, and will be described as including particular materials and/or components herein, it will be understood that one or more additional components may be added, that one or more components may be removed, that combinations of components may be combined to perform similar operations, and that the components may be comprised of multiple sub-components that are not depicted or described herein.

Various interconnections between components of gas sensor 100 as well as additional circuitry such as processing circuitry are not depicted in the exploded view of FIG. 1, but will be understood to be present in gas sensor 100 and/or other components or circuits connected thereto. For example, components such as heating elements (e.g., heating elements 106a-106b), electrodes (e.g., electrodes 110a-110c), and sensing elements (e.g., gas detection element thermistor 112a and reference element thermistor 112b-112c) may all be connected to other components such as processing circuitry to monitor and control such components.

In an exemplary embodiment, processing circuitry may include one or more components providing necessary processing based on the requirements of the gas sensor 100. Processing circuitry may include hardware control logic that may be integrated within gas sensor 100 (e.g., a CMOS layer located adjacent to wafer 102) or other chips or components (e.g., integrated or adjacent ASICs) in communication with gas sensor 100. Processing circuitry may also include a processor such as a microprocessor that executes software instructions, e.g., that are stored in a memory. The microprocessor may control the operation of gas sensor 100 directly and/or by interacting with hardware control logic of gas sensor 100, and process signals received by gas sensor 100.

In an embodiment of the present disclosure, wafer 102 may have a relatively large height and size in comparison to the other layers and components of gas sensor 100. The wafer may include an insulating structural material such as silicon and may provide physical support for the other components of gas sensor 100 to facilitate placement of gas sensor 100 in an appropriate environment and interconnection of gas sensor 100 with other mechanical and electrical components and systems of an end-use device in which gas sensor 100 is integrated.

In an embodiment, thermal film 104 (e.g., of material such as silicon dioxide) may be attached to wafer 102 between wafer 102 and heating elements 106a-106b. The heating elements may be configured to be heated to particular temperatures and/or may be coupled to circuitry such as processing circuitry to selectively control the temperature of respective heating elements 106a and 106b. Although heating elements 106a and 106b may comprise a variety of materials, and some embodiments may be different to better achieve different particular temperature ranges for gas detection element 112a and reference elements 112b-112c, in an exemplary embodiment heating elements 106a-106b may include layers of titanium and platinum, although other exemplary heater materials include platinum, tungsten, copper, polysilicon, and/or other conducting materials. In some embodiments, feedback regarding the temperature and operation of the heating elements 106a-106b may be provided from heating elements 106a-106b, measured by additional circuitry in proximity to heating elements 106a-106b, or determined based on components that are electrically connected to heating elements 106A-106B (e.g., based on voltage or current).

Insulating film 108 (e.g., of silicon dioxide) may be located between heating elements 106a-106b and sensing elements 112a-112c and associated electrodes 110a-110c, with appropriate access and patterning to facilitate the provision of heat to sensing elements 112a-112c from heating elements 106a-106b. As described herein, heating element 106a may be associated with gas detection element 112a (e.g., thermistor 112a, such as a MnCoNi Oxide thermistor or oxides of manganese, nickel, cobalt, and/or iron) to heat gas detection element 112a to a temperature that is suitable for the detection of a gas of interest (e.g., CO or $CO_2$), while heating element 106b may be associated with reference elements 112b-112c (e.g., thermistors 112b-112c, such as MnCoNi Oxide thermistors) to heat reference elements 112b-112c to a temperature that is suitable for the detection of conditions (e.g., water vapor/humidity) to be offset or removed from the output of gas detection element 112a. An additional insulating film 114 (e.g., of silicon dioxide) may partially cover sensing elements 112a-112c and have electrode pads 116 located thereon which form electrical connections with electrodes 110a-110c via sensing elements 112a-112c to facilitate measurement and monitoring of sensing elements 112a-112c (e.g., by measuring changes in resistance due to interaction with a gas of interest or other conditions). Although not depicted in FIG. 1, electrodes 110a-110c may provide connections to processing circuitry that interconnects gas detection element 112a and reference elements 112b-112c, connects these components to other circuitry, and determines quantities of a gas of interest.

Figure 2:
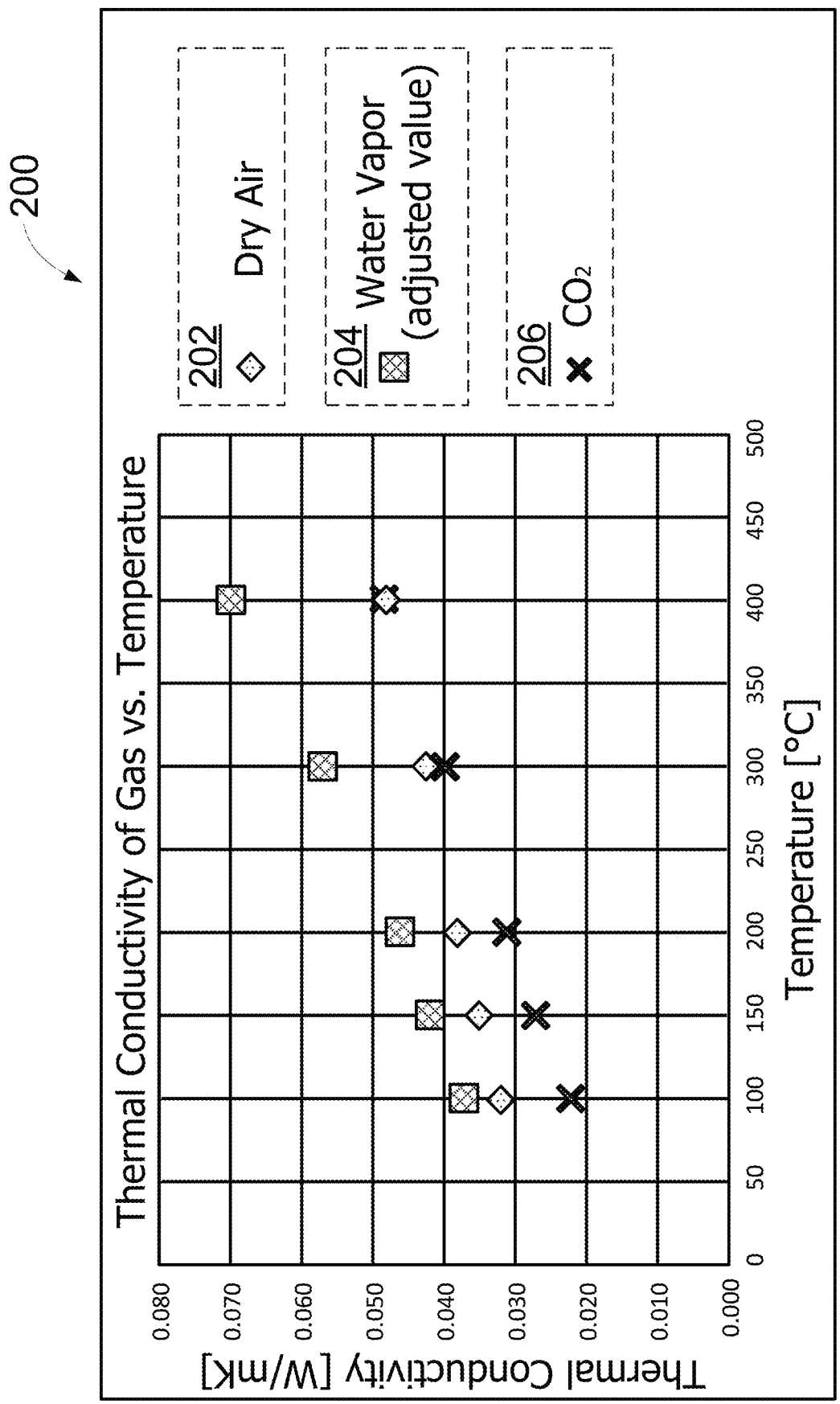
FIG. 2 depicts an exemplary thermal conductivity response of a gas sensor in response to a gas of interest and to different humidity levels in accordance with some embodiments of the present disclosure.

FIG. 2 depicts an exemplary thermal conductivity response of a gas sensor in response to a gas of interest and to different humidity levels in accordance with some embodiments of the present disclosure. The x-axis of FIG. 2 represents temperature and is in units of degrees Celsius while the y-axis represents thermal conductivity and is in units of watts per meter-Kelvin. The exemplary relationships depicted in FIG. 2 relate to a particular MnCoNi Oxide based thermistor used to detect a gas of interest of $CO_2$ in the presence of humidity that affects the sensor output. It will be understood that other sensor types, sensor configurations, gasses of interest, and other conditions may result in different temperature vs. thermal conductivity profiles and responses.

FIG. 2 depicts the thermal conductivity of the gas at various temperatures in the presence of dry air (diamonds, indicated with reference numeral 202), water vapor ("adjusted value" in squares, indicated with reference numeral 204) and $CO_2$ ("X", indicated by reference numeral 206). Dry air corresponds to approximately 0% humidity, for example, less than 1% or 0.5% humidity. The adjusted value for water vapor represents water vapor mixed in air to an extent to which the polar nature of the water molecules affects the thermal conductivity of the mixture and behaves as if the thermal conductivity of water vapor in the mixture is more than pure water vapor. As depicted in FIG. 2, at a temperature of 100° C., a volume of dry air has a thermal conductivity of approximately 0.032 W/mK. In the presence of pure $CO_2$, the thermal conductivity drops to approximately 0.021 W/mK. Thermal conductivity changes due to changes in the gas constituents result in changes in thermistor resistance that can be measured. However, when humidity is present at 100° C., the thermal conductivity of the gas increases (e.g., to 0.038 W/mK at 100% humidity). As a result, changes in humidity may partially obscure the output of the thermistor relating to the gas of interest (e.g., $CO_2$).

Similar responses to humidity and $CO_2$ can be seen when the thermistor is heated to 150° C. and 200° C., respectively, with the impact of $CO_2$ on the thermal conductivity slowly decreasing while the impact of humidity on the thermal conductivity increases. In this manner, as the temperature of the exemplary MnCoNi Oxide thermistor increases, the presence of humidity further obscures the change in thermal conductivity due to the gas of interest (e.g., $CO_2$). Once the thermistor achieves a temperature of 300° C., the effect of humidity on the thermal conductivity is dominant compared to the effect of $CO_2$. At a thermistor temperature of 400° C., the effect of $CO_2$ on thermal conductivity is essentially zero.

Figure 3A:
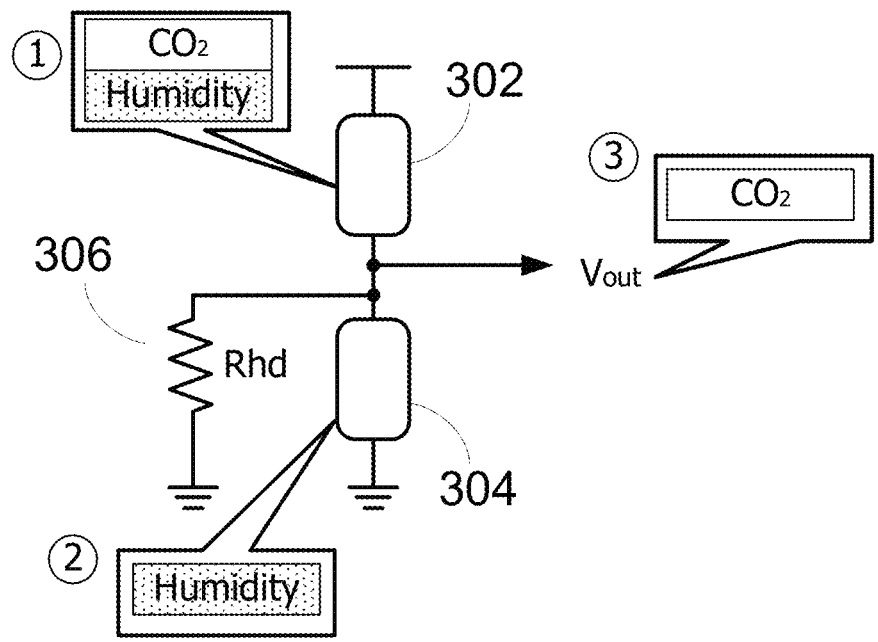
FIG. 3A depicts an exemplary diagram of a configuration for removing humidity effects from the output of a gas sensor in accordance with some embodiments of the present disclosure.
Figure 3B:
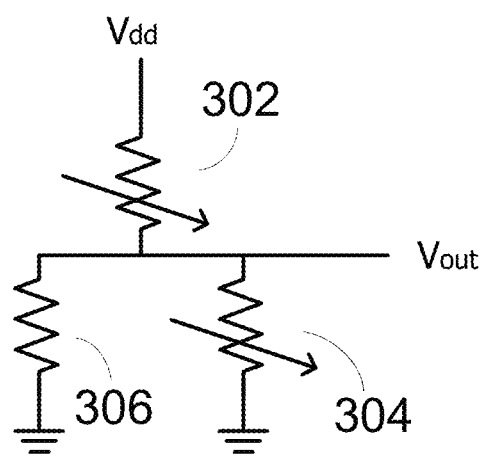
FIG. 3B depicts an exemplary schematic of the configuration of FIG. 3A in accordance with some embodiments of the present disclosure.

FIG. 3A depicts an exemplary diagram of a configuration for reducing humidity effects in the output of a gas sensor in accordance with some embodiments of the present disclosure, while FIG. 3B depicts an exemplary schematic of the configuration of FIG. 3A in accordance with some embodiments of the present disclosure. In the exemplary embodiment of FIGS. 3A and 3B, gas detection element 302 (e.g., a MnCoNi Oxide thermistor as represented by variable resistor 302 in FIG. 3B) is heated to a temperature (e.g., 150° C.) at which it is primarily responsive to a gas of interest (e.g., $CO_2$), but at which humidity also impacts the conductivity of gas detection element 302.

In an exemplary embodiment, a reference element 304 may have a similar (e.g., identical) size, shape, and specifications as gas detection element 302 (e.g., a MnCoNi Oxide thermistor as represented by variable resistor 304 in FIG. 3B) and may be heated to a temperature (e.g., 300° C.) at which the effect due to a gas of interest (e.g., $CO_2$) is substantially zero, but at which the effect of humidity on the thermal conductivity of reference element 304 is substantial. In this manner, reference element 304 may have a resistance that varies almost exclusively based on the humidity of the gas being measured.

Fixed resistor Rhd 306 may be connected in parallel with reference element 304 to provide scaling between the humidity effects at the temperature of gas detection element 302 and reference element 306. If scaled properly, any change (e.g., increase in thermal conductivity as humidity increases, and decrease in resistance) in the resistance of gas detection element 302 due to an increase in humidity is reduced by a corresponding change in resistance to reference element 304. Thus, an output (Vout) at a connecting node between gas detection element 302 and reference element 304 may mostly represent the concentration of the gas of interest (e.g., $CO_2$) with the effects of other conditions (e.g., humidity) reduced.

In other embodiments (not depicted in FIGS. 3A-3B), scaling may be performed by other circuitry such as processing circuitry. For example, rather than connecting gas detection element 302 and reference element 304 to a common connecting node, the outputs of these elements may be provided separately to additional analog and/or digital components for scaling and removal of humidity effects to isolate the response to the gas of interest.

Figure 4:
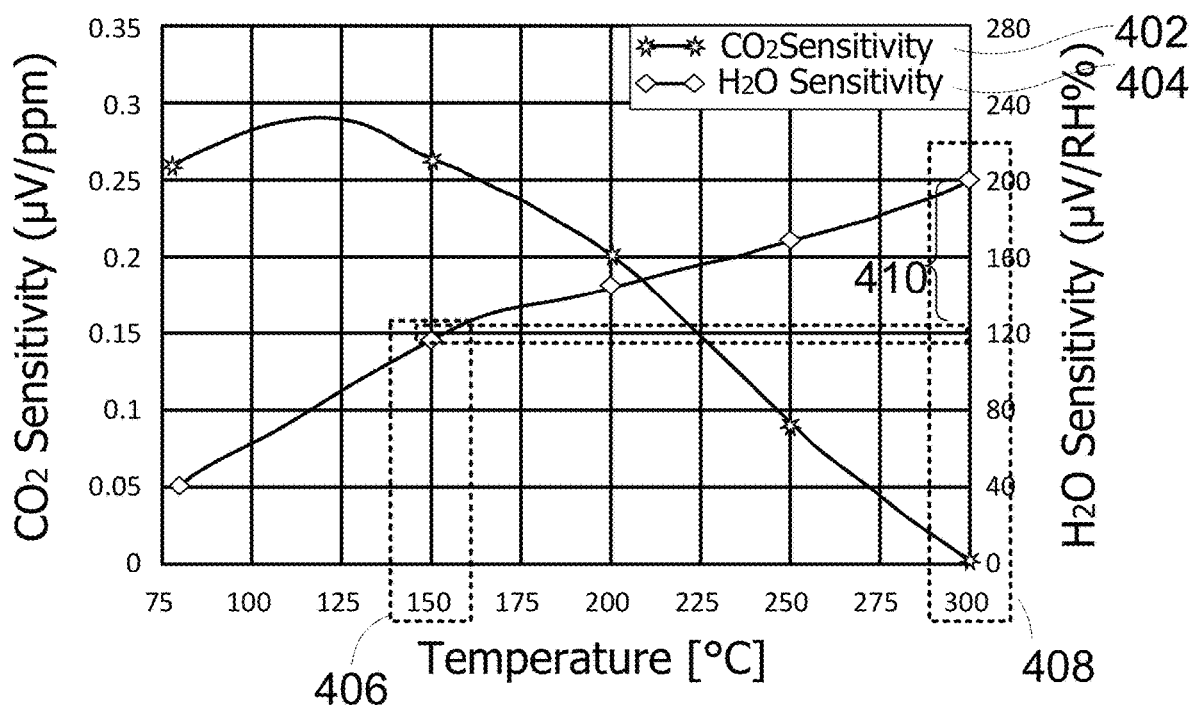
FIG. 4 depicts exemplary sensitivity characteristics of the gas sensor of FIG. 3A to a gas of interest and humidity for use in selecting a resistance value in accordance with some embodiments of the present disclosure.

FIG. 4 depicts exemplary sensitivity characteristics of the gas sensor if FIG. 3A to a gas of interest and humidity for use in selecting a matched resistance value (e.g., Rhd 306) in accordance with some embodiments of the present disclosure. Sensitivity 402 of an exemplary thermistor (e.g., a MnCoNi Oxide thermistor) to $CO_2$ and sensitivity 404 of the exemplary thermistor to humidity are depicted in FIG. 4. In the exemplary embodiment of FIGS. 3A-3B, temperature 406 of a gas detection element may be 150° C., at which the sensitivity of gas detection element 302 to $CO_2$ is at a relatively high point and the sensitivity to humidity is relatively low, but there is still a substantial response to humidity. Temperature 408 of reference element 304 may be 300° C., at which the sensitivity to $CO_2$ is essentially zero while the sensitivity to humidity is substantial and greater than the sensitivity at 150° C. Offset 410 between the humidity sensitivity at temperature 406 versus the humidity sensitivity at temperature 408 may be used to select parallel resistor 306 or other scaling circuitry, allowing similar sensing elements to be used for gas detection element 302 and reference element 304, thereby limiting the possibility of mismatch between the two sensing elements negatively impacting the accuracy of humidity removal and gas detection.

Figure 5:
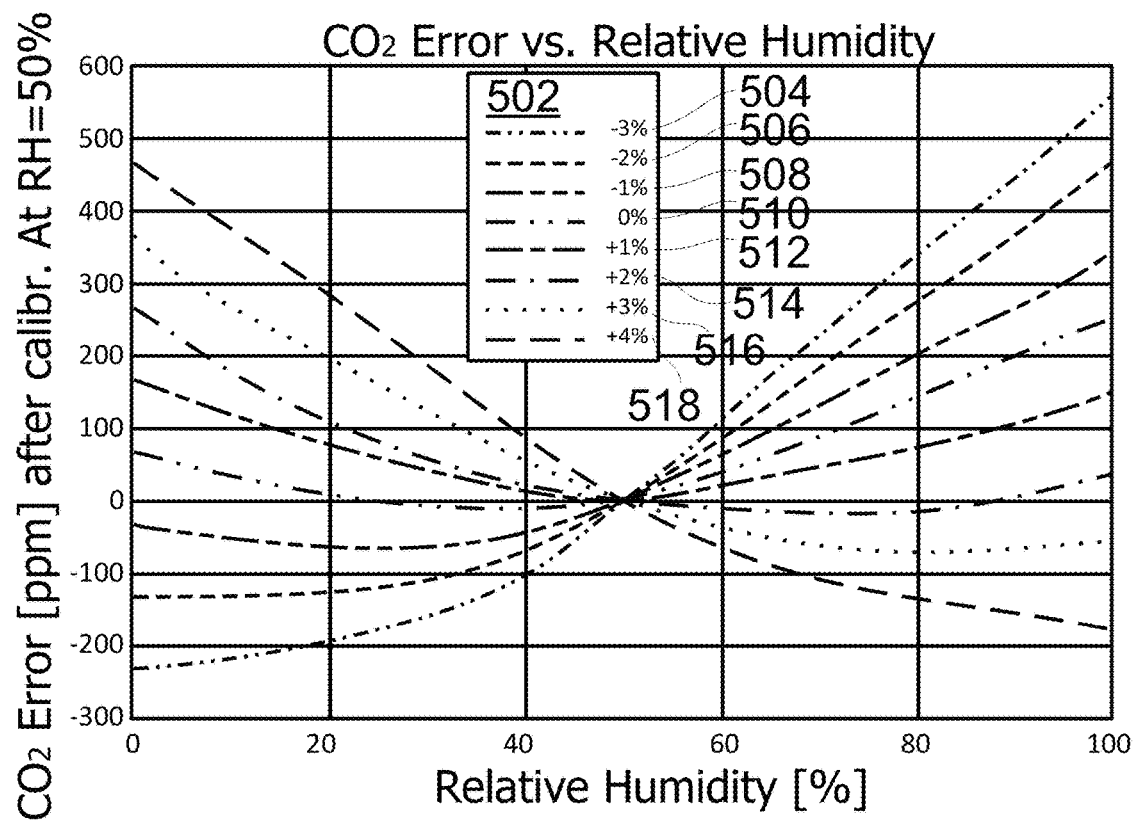
FIG. 5 depicts exemplary sensitivity errors in response to different degrees of mismatch between a humidity sensing element and a resistive element in accordance with some embodiments of the present disclosure.

FIG. 5 depicts exemplary sensitivity errors in response to different degrees of mismatch between a humidity sensing reference element and a resistive element (e.g., of FIGS. 3A-3B) in accordance with some embodiments of the present disclosure. As described with respect to FIG. 4, the selection of an appropriate resistor value and configuration (e.g., a parallel resistor having a resistance sized to account for the difference between the sensitivity to humidity of a particular thermistor at the temperature of the reference element and the sensitivity to humidity of an similar thermistor at the temperature of the gas detection element) can provide proper scaling that at least partially offsets any impact of humidity on the output of the gas detection element.

The selection of the resistor value (e.g., Rhd) is performed under certain conditions, such as particular temperatures for the sensing elements as well as the base humidity experienced while the resistor value is being calculated. Offset 410 of FIG. 4 will be different for different humidity levels, at least in part because the fixed resistor (e.g., Rhd) does not change with humidity in the same manner as the reference element (e.g., MnCoNi Oxide thermistor). Furthermore, there are variations in sensing elements and resistors, and even typical tolerances can result in 2-3% mismatch compared to ideal resistor and sensing element values and characteristics. FIG. 5 depicts these effects and assumes that the calibration of offset 410 was performed at 50% relative humidity. As depicted in FIG. 5, even with a perfect match between the resistor and reference element (i.e., 0% error plotted as line 510), the further the relative humidity departs from the humidity used during calibration, the greater the error in the measured gas of interest (e.g., $CO_2$). For example, with 0% mismatch (line 510), the error can range from approximately 80 ppm (at 0% humidity) to approximately 250 ppm (at 100% humidity). Where a mismatch occurs (e.g., lines 504-508 and 512-518), these errors increase to 500 ppm or above.

Figure 6A:
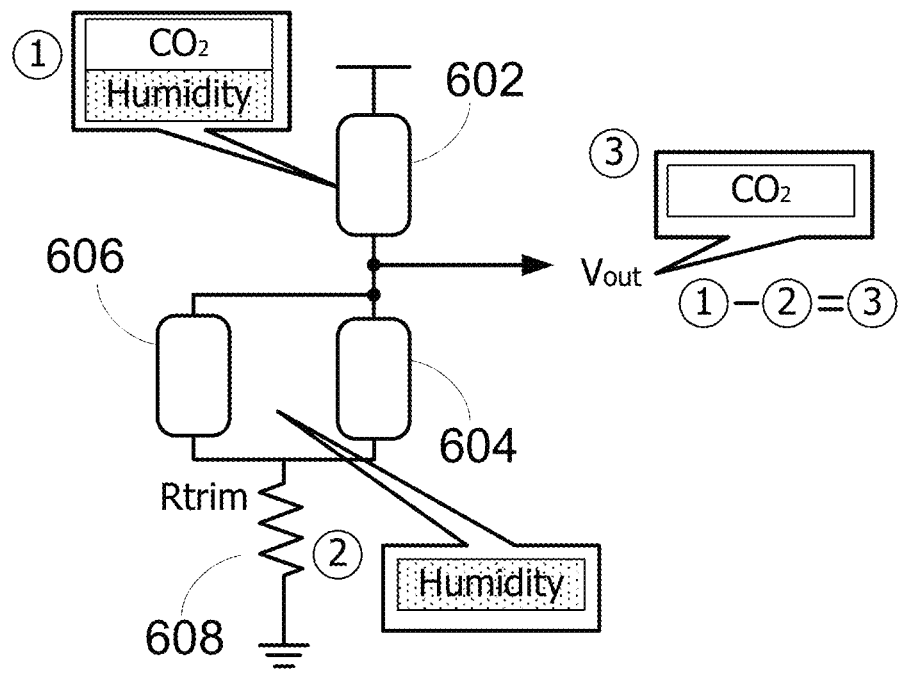
FIG. 6A depicts an exemplary diagram of a configuration for removing humidity effects from the output of a gas sensor using a reference element network in accordance with some embodiments of the present disclosure.
Figure 6B:
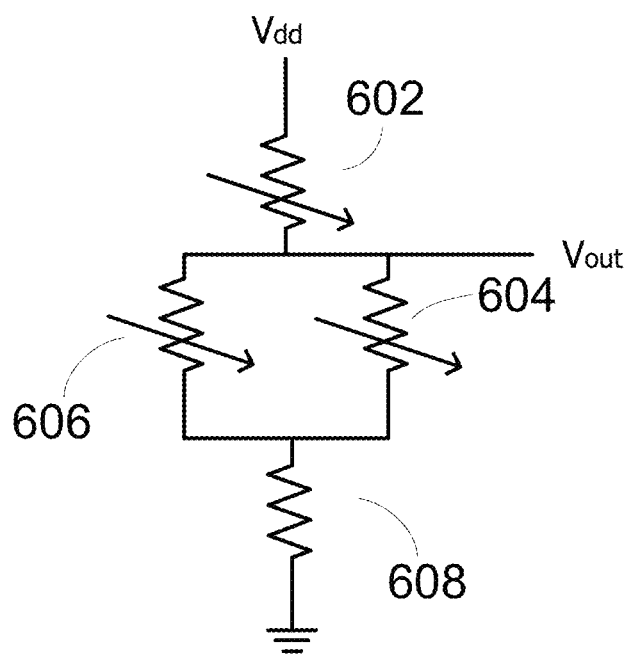
FIG. 6B depicts an exemplary schematic of the configuration of FIG. 6A in accordance with some embodiments of the present disclosure.

FIG. 6A depicts an exemplary diagram of a configuration for removing humidity effects from the output of a gas sensor using a reference element network in accordance with some embodiments of the present disclosure, while FIG. 6B depicts an exemplary schematic of the configuration of FIG. 6A in accordance with some embodiments of the present disclosure. In the exemplary embodiment of FIGS. 6A and 6B, gas detection element 602 (e.g., a MnCoNi Oxide thermistor as represented by variable resistor 602 in FIG. 6B) is heated to a temperature (e.g., 130° C.) at which it is primarily responsive to a gas of interest (e.g., $CO_2$), but at which humidity also impacts the conductivity of the gas detection element 602.

In an exemplary embodiment, parallel-connected reference elements 604 and 606 may have similar (e.g., identical) size, shape, and specifications as gas detection element 602 (e.g., MnCoNi Oxide thermistors as represented by variable resistors 604 and 606 in FIG. 3B) and may be heated to a temperature (e.g., 300° C.) at which the effect due to a gas of interest (e.g., $CO_2$) is substantially zero, but at which the effect of humidity on the conductivity of reference elements 604 and 606 is substantial. In this manner, reference elements 604 and 606 may have a resistance that varies almost exclusively based on the humidity of the volume of gas being measured.

The reference elements may be connected in a reference element network in order to properly offset the humidity effect on gas detection element 602 at the heated temperature (e.g., 130° C.). A variety of numbers of reference elements, reference element types, and reference element configurations may be utilized to successfully offset a particular humidity (or other) effect on measurement of a gas of interest. For example, multiple banks of reference elements may be coupled in parallel and/or series and may be switched in and out of the reference element network (e.g., based on changed offsets due to changes in temperature of a gas detection element, or switching out of different gas detection elements having different characteristics). In some embodiments, a plurality of lower (nominal) resistance reference elements may be used for fine tuning of the offset, for example, based on calibration routines where the gas sensor is exposed to known concentrations of a gas of interest and other conditions (e.g., humidity).

In the exemplary embodiment of FIGS. 6A-6B, reference elements 604 and 606 are identical reference elements that are connected in parallel. Because reference elements 604 and 606 are configured in a reference element network and change with humidity in a similar manner, errors due to any potential mismatch due to manufacturing tolerances are reduced, as compared to a fixed resistor that is relatively insensitive to humidity. In addition, in some embodiments, a trim resistor may be connected to the reference element network (e.g., between the reference element network and ground as depicted in FIGS. 6A-6B). The trim resistor may be used for linear scaling to a desired Vout value (e.g., based on respective changes in the gas detection element 602 and reference element network of reference elements 604 and 606). Such a trim resistor could be placed in different configurations in the reference element network (i.e. in a parallel configuration versus the series configuration shown in FIGS. 6A-6B).

Figure 7:
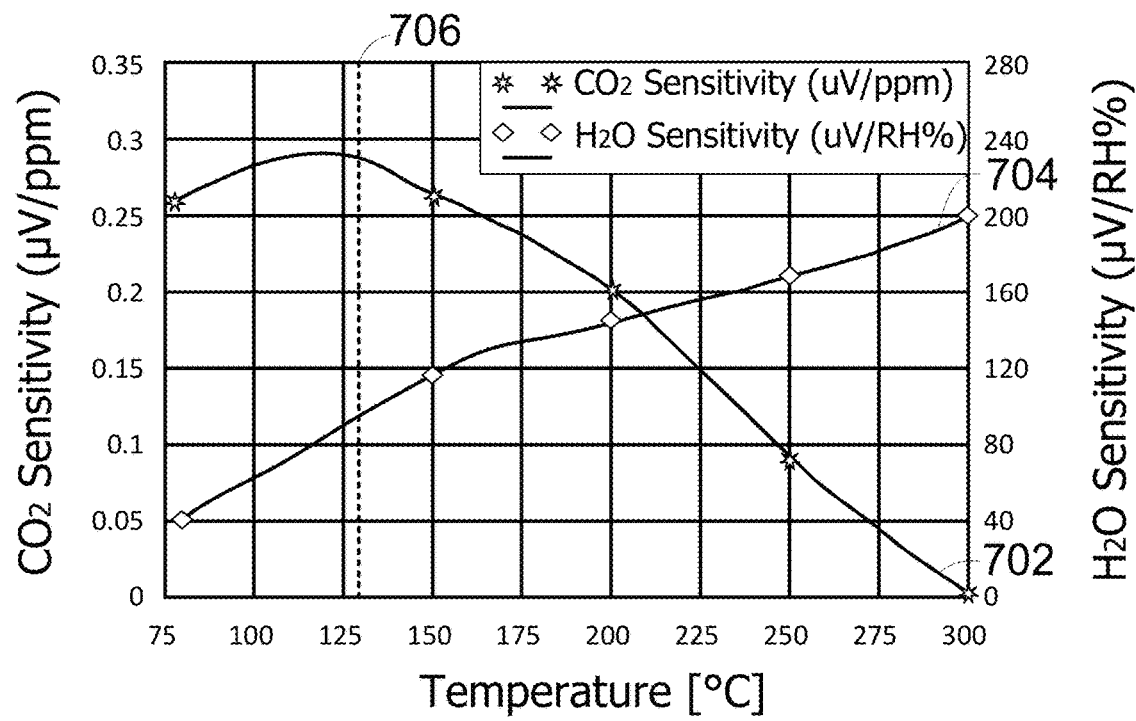
FIG. 7 depicts exemplary sensitivity characteristics of the gas sensor of FIG. 6A to a gas of interest and humidity in accordance with some embodiments of the present disclosure.

FIG. 7 depicts exemplary sensitivity characteristics of the gas sensor of FIG. 6A to a gas of interest and humidity in accordance with some embodiments of the present disclosure. It may be desirable to choose operating temperatures for the gas detection element (e.g., gas detection element 602) and reference elements (e.g., reference elements 604 and 606) in a manner that limits errors that may result from different concentrations of other conditions (e.g., humidity) that impact thermal conductivity as well as mismatch between components (e.g., as a result of manufacturing tolerances and/or changes during operation).

In some embodiments, temperatures may be selected for particular sensing elements based on a known sensitivity of the particular sensing elements to the gas of interest (e.g., $CO_2$) and other conditions (e.g., humidity) that impact the sensor response. As is depicted in FIG. 7, an exemplary sensing element (e.g., a MnCoNi Oxide thermistor) has $CO_2$ sensitivity 702 and $H_2O$ sensitivity 704 over a range of temperatures from 75° C. to 300° C. In an exemplary embodiment, an exemplary operating temperature for a gas detection element (e.g., a thermistor gas detection element 602) may be selected at a temperature where the slope of $CO_2$ sensitivity 702 is close to zero, such as at 130° C. as indicated by intercept line 706. In this manner, minor variations in temperature and/or construction of the gas detection element may have a limited impact on the portion of the output of the gas detection element that is attributable to the gas of interest. A temperature for the reference elements may be selected at a temperature at which the sensitivity to the gas of interest approaches zero (e.g., for $CO_2$ sensitivity 702) and the other condition (e.g., $H_2O$ sensitivity 704) can be accurately measured.

Scaling between the selected temperatures—e.g., to properly account for the difference in sensitivity to the other condition (e.g., as indicated by $H_2O$ sensitivity 704) can be performed based on the selection and configuration of the reference element network and trim resistor. In some embodiments, the reference element network and gas detection element can be selected, and the temperatures applied to the gas detection element and reference element network adjusted to arrive at temperatures to provide the proper scaling. In some embodiments, temperatures may be updated dynamically during operation of the gas sensor, for example, based on periodic calibration routines under known conditions. In another example, temperature may be changed based on auxiliary inputs from other sensors such as pressure, humidity, and/or external temperature.

Figure 8:
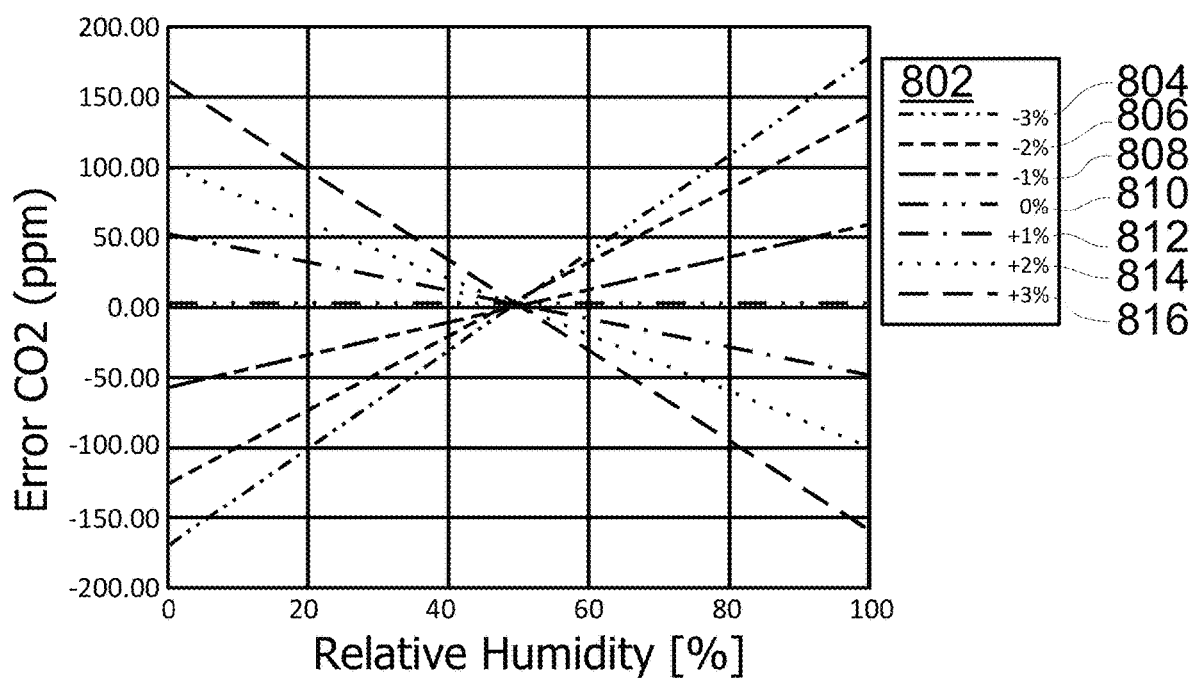
FIG. 8 depicts exemplary sensitivity errors in response to different degrees of mismatch between sensing elements in accordance with some embodiments of the present disclosure.

FIG. 8 depicts exemplary sensitivity errors in response to different degrees of mismatch between sensing elements in accordance with some embodiments of the present disclosure. The exemplary embodiment of FIG. 8 corresponds to the reference element network and gas detection element configuration of FIGS. 6A-6B, having characteristics of the MnCoNi Oxide thermistor of FIG. 7.

The selection of the sensing element types and temperatures is performed under certain conditions, such as the base humidity experienced while the temperature is being selected. For example, there are variations in sensing elements and resistors, and even typical tolerances can result in 2-3% mismatch compared to ideal sensing element values and characteristics. FIG. 8 depicts these effects for the configuration of FIGS. 6A-6B and 7, and assumes that the temperature selection was performed at 50% relative humidity. As depicted in FIG. 8, with a perfect match between the reference elements and gas detection element (i.e., 0% error plotted as line 810), the error is approximately zero even at different relative humidity levels (e.g., based on the reference elements and gas elements all changing in response to the changes in humidity). Where a component mismatch occurs (e.g., lines 804-808 and 812-816), the $CO_2$ errors are relatively low except at extremes of 0% and 100% humidity, and even then, are far less than the errors as described for FIG. 5 herein.

Figure 9:
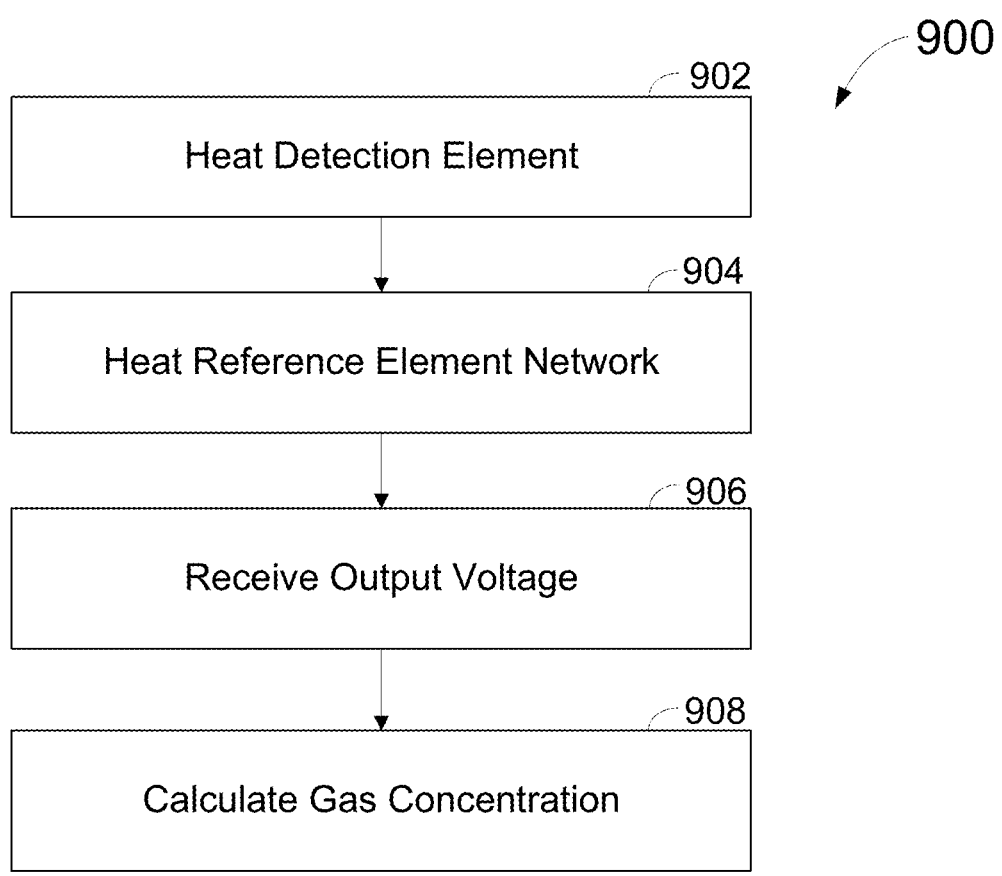
FIG. 9 depicts exemplary steps for operating a gas sensor in accordance with some embodiments of the present disclosure.

FIG. 9 depicts exemplary steps for operating a gas sensor in accordance with some embodiments of the present disclosure. Although FIG. 9 is described in the context of the present disclosure, it will be understood that the methods and steps described in FIG. 9 may be applied to a variety of gas sensor designs, sensing element types, processing circuitry, and measurement techniques. Although a particular order and flow of steps is depicted in FIG. 9, it will be understood that in some embodiments one or more of the steps may be modified, moved, removed, or added, and that the flow depicted in FIG. 9 may be modified.

At step 902, a gas detection element (e.g., a MnCoNi Oxide thermistor) may be heated to a temperature that is suitable for measurement of a gas of interest. For example, as described herein, the temperature that the gas detection element is heated to may correspond to a temperature at which the gas detection is sensitive to changes in the concentration of a gas of interest (e.g., $CO_2$) and at which the sensitivity is relatively stable in response to typical variances in gas detection element manufacture or design (e.g., near a low or zero slope area of a sensitivity curve for a gas of interest). Once the gas detection element has been heated to the appropriate temperature, processing may continue to step 904.

At step 904, the reference element network (e.g., two parallel connected MnCoNi Oxide thermistors) may be heated to a temperature that is suitable for measurement of other conditions (e.g., humidity), for example, based on a temperature at which any changes to the reference element network (e.g., changes in resistance) are primarily due to the other condition. Once the reference elements of the reference element network are heated to the appropriate temperature, processing may continue to step 906.

At step 906, one or more output voltages associated with the gas detection element and reference element may be received, e.g., by processing circuitry. For example, the gas detection element and reference element network may be configured as a voltage divider in which the output voltage corresponds to a connecting node between the gas detection element and the reference element network. Changes to the gas detection element (e.g., changes in resistance) may correspond to the concentration of the gas of interest (e.g., $CO_2$) and the other condition (e.g., humidity) and changes in the reference element network (e.g., due to humidity) may offset any change in the gas detection element that is not due to the gas of interest. In this manner, changes to the output voltage corresponding to the connecting node may correspond to changes in the concentration of the gas of interest. Processing may then continue to step 908.

At step 908, the concentration of the gas of interest may be calculated based on the output value (e.g., the voltage of the connecting node). For example, a set of look-up values may correspond to particular sensing elements and heater temperatures, and may be used to calculate the gas concentration. Once the gas concentration has been calculated, processing may continue or wait until the next appropriate (e.g., periodic) monitoring event.

The foregoing description includes exemplary embodiments in accordance with the present disclosure. These examples are provided for purposes of illustration only, and not for purposes of limitation. It will be understood that the present disclosure may be implemented in forms different from those explicitly described and depicted herein and that various modifications, optimizations, and variations may be implemented by a person of ordinary skill in the present art, consistent with the following claims.

What is claimed is:

1. A sensor for measuring a concentration of a gas of interest, comprising:
   a gas detection element;
   a reference element network comprising a plurality of reference elements, wherein each reference element of the plurality of reference elements is coupled to another reference element of the plurality of reference elements;
   one or more heating elements, wherein the one or more heating elements cause the gas detection element to operate at a first temperature at which the gas detection element is sensitive to the gas of interest and wherein the one or more heating elements cause the plurality of reference elements to operate at a second temperature at which the reference element network is not sensitive to the gas of interest; and
   processing circuitry coupled to the gas detection element and the reference element network, wherein the processing circuitry is configured to determine a value corresponding to the concentration of the gas of interest based on one or more signals received from the gas detection element and the reference element network.

2. The sensor of claim 1, wherein each of the plurality of reference elements is fabricated to have the same size and shape.

3. The sensor of claim 2, wherein each of the plurality of reference elements is fabricated from the same materials.

4. The sensor of claim 3, wherein the gas detection element is fabricated from the same materials as the plurality of reference elements.

5. The sensor of claim 4, wherein the gas detection element is fabricated to have the same size and shape as the plurality of reference elements.

6. The sensor of claim 1, wherein each of the plurality of reference elements are coupled in parallel to each other or in series.

7. The sensor of claim 1, wherein the second temperature is a temperature at which the reference element network is sensitive to humidity.

8. The sensor of claim 7, wherein the gas detection element and the reference element network are coupled in a bridge configuration.

9. The sensor of claim 7, wherein a change in a value of the gas detection element due to a change in humidity is offset by a corresponding change in a value of the reference element network.

10. The sensor of claim 9, wherein the change and the corresponding change substantially eliminate any effect of humidity on the value corresponding to the concentration of the gas of interest.

11. The sensor of claim 7, wherein the gas detection element and the reference element network are connected in series, and wherein the value corresponding to the concentration of the gas of interest is proportional to a voltage at a connecting node between the gas detection element and the reference element network.

12. The sensor of claim 11, further comprising a trim element coupled between the reference element network and a reference voltage.

13. The sensor of claim 12, wherein the reference voltage is ground, wherein a second voltage is applied to the gas detection element at an opposite node from the connecting node, and wherein the gas detection element, reference element network, and trim element are coupled in series between the second voltage and ground.

14. The sensor of claim 1, wherein the gas detection element and each of the plurality of reference elements or the detector element comprise a thermistor.

15. The sensor of claim 14, wherein the thermistors each comprise a MnCoNi oxide material.

16. The sensor of claim 1, wherein the sensitivity of the gas detection element to the gas of interest changes based on an applied temperature of the gas detection element, and wherein the first temperature corresponds to an applied temperature at which the slope of the sensitivity of the gas detection element is substantially zero.

17. The sensor of claim 1, wherein the gas of interest comprises carbon dioxide.

18. A method for measuring a concentration of a gas of interest, comprising:
   applying, by a first heating element, a first temperature to a gas detection element, wherein the gas detection element is sensitive to the gas of interest at the first temperature;
   applying, by at least one second heating element, a second temperature to a reference element network comprising a plurality of reference elements, wherein the reference element network is not sensitive to the gas of interest at the second temperature; and
   determining, by processing circuitry coupled to the gas detection element and the reference element network, a value corresponding to the concentration of the gas of interest based on one or more signals received from the gas detection element and the reference element network.

19. The method of claim 18, wherein the reference element network is sensitive to humidity at the second temperature, and wherein a change in a value of the gas detection element due to a change in humidity is offset by a corresponding change in a value of the reference element network.

20. A sensor for measuring a concentration of a gas of interest, comprising:
  a gas detection element;
  a reference element network coupled to the gas detection element at a connecting node, the reference element network comprising a plurality of reference elements;
  one or more heating elements, wherein the one or more heating elements cause the gas detection element to operate at a first temperature at which the gas detection element is sensitive to the gas of interest and wherein the one or more heating elements cause the plurality of reference elements to operate at a second temperature at which the reference element network is sensitive to humidity and is not sensitive to the gas of interest; and
  processing circuitry coupled to the connecting node, wherein the processing circuitry is configured to determine a value corresponding to the concentration of the gas of interest based on an output signal from the connecting node.

* * * * *